(12) United States Patent
Alisantoso et al.

(10) Patent No.: US 8,974,414 B2
(45) Date of Patent: Mar. 10, 2015

(54) IV DRIP CHAMBER WITH FILTER AND BOTTOM RESERVOIR

(71) Applicant: Becton, Dickinson and Company, Franklin Lakes, NJ (US)

(72) Inventors: Darius Alisantoso, Singapore (SG); Kiat Jin Cheng, Singapore (SG); Kevin Neo, Singapore (SG)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 13/766,529

(22) Filed: Feb. 13, 2013

(65) Prior Publication Data

US 2014/0228806 A1 Aug. 14, 2014

(51) Int. Cl.
*A61M 1/00* (2006.01)
*A61M 5/38* (2006.01)
*A61M 5/14* (2006.01)

(52) U.S. Cl.
CPC ............... *A61M 5/38* (2013.01); *A61M 5/1411* (2013.01)
USPC ........... 604/126; 604/406; 604/256; 604/403; 604/405; 604/252

(58) Field of Classification Search
USPC .................. 604/126, 406, 256, 403, 405, 252
See application file for complete search history.

(56) References Cited

U.S. PATENT DOCUMENTS

| | | | |
|---|---|---|---|
| 3,390,677 A | 7/1968 | Razimbaud | |
| 3,631,654 A | 1/1972 | Riely et al. | |
| 3,722,697 A * | 3/1973 | Burke et al. | 210/451 |
| 4,004,587 A * | 1/1977 | Jess | 604/126 |
| 4,013,072 A | 3/1977 | Jess | |
| 4,031,891 A * | 6/1977 | Jess | 604/126 |
| 4,173,222 A | 11/1979 | Muetterties | |
| 4,198,971 A | 4/1980 | Noiles | |
| 4,200,095 A | 4/1980 | Reti | |
| 4,227,525 A * | 10/1980 | Lundquist | 604/126 |
| 4,227,527 A | 10/1980 | De Frank et al. | |
| 4,396,016 A | 8/1983 | Becker | |
| 4,571,244 A | 2/1986 | Knighton | |
| 4,615,694 A | 10/1986 | Raines | |
| 4,685,912 A | 8/1987 | Jones | |
| 4,906,260 A | 3/1990 | Emheiser et al. | |
| 5,242,424 A | 9/1993 | Chen | |
| 5,290,253 A | 3/1994 | Kira | |

(Continued)

FOREIGN PATENT DOCUMENTS

DE 966756 C 9/1957
EP 0 001 114 A2 3/1979

(Continued)

OTHER PUBLICATIONS

Braun, Product detail, http://www.bbraunoem-industrial.com/products/details.cfm?prodid=B0843225&id=Caps&area=C, p. 1, Apr. 12, 2005.

*Primary Examiner* — Scott Medway
(74) *Attorney, Agent, or Firm* — Jeanne Lukasavage; Craig Metcalf; Kirton McConkie

(57) ABSTRACT

A drip chamber having an upper reservoir that is separated from a lower reservoir via a filter assembly, wherein a distance between the filter assembly and a bottom surface of the drip chamber is selected to prevent dislodged air bubbles of the filter assembly from being drawn into an intravenous fluid line that is coupled to the bottom surface of the drip chamber, during an infusion procedure.

7 Claims, 4 Drawing Sheets

(56) References Cited

U.S. PATENT DOCUMENTS

| | | |
|---|---|---|
| 5,308,314 A | 5/1994 | Fukui et al. |
| 5,423,346 A | 6/1995 | Daoud |
| 5,489,385 A | 2/1996 | Raabe et al. |
| 5,603,706 A | 2/1997 | Wyatt et al. |
| 5,779,674 A | 7/1998 | Ford |
| 5,855,230 A | 1/1999 | Guala et al. |
| 5,902,281 A * | 5/1999 | Kraus et al. ............ 604/251 |
| 5,954,957 A | 9/1999 | Chin-Loy et al. |
| 6,013,061 A | 1/2000 | Kelley |
| 6,261,267 B1 | 7/2001 | Chen |
| 6,336,916 B1 | 1/2002 | Bormann et al. |
| 6,468,251 B1 | 10/2002 | Yamanaka et al. |
| 6,699,215 B2 | 3/2004 | Fujii |
| 6,972,000 B2 | 12/2005 | Kappel et al. |
| 7,722,577 B2 | 5/2010 | Miner |
| 8,282,608 B2 | 10/2012 | Miner et al. |
| 2002/0156431 A1 | 10/2002 | Feith et al. |
| 2005/0171491 A1 | 8/2005 | Minh Miner et al. |
| 2011/0276031 A1 | 11/2011 | Hoang et al. |

FOREIGN PATENT DOCUMENTS

| | | |
|---|---|---|
| WO | 01/41844 A1 | 6/2001 |
| WO | 2004/020037 A1 | 3/2004 |

\* cited by examiner

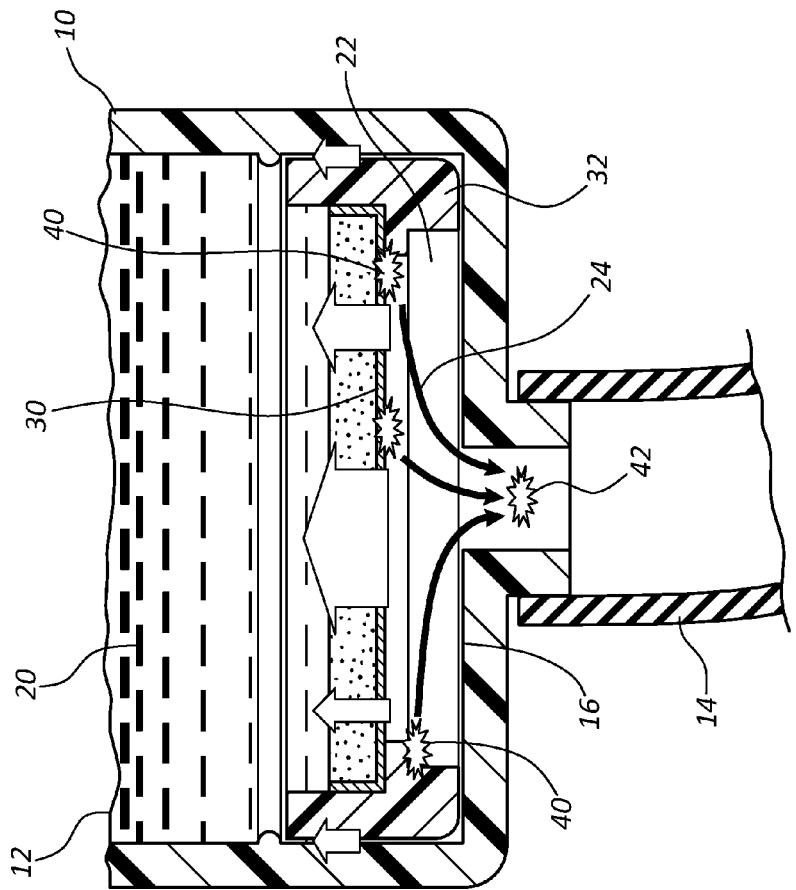
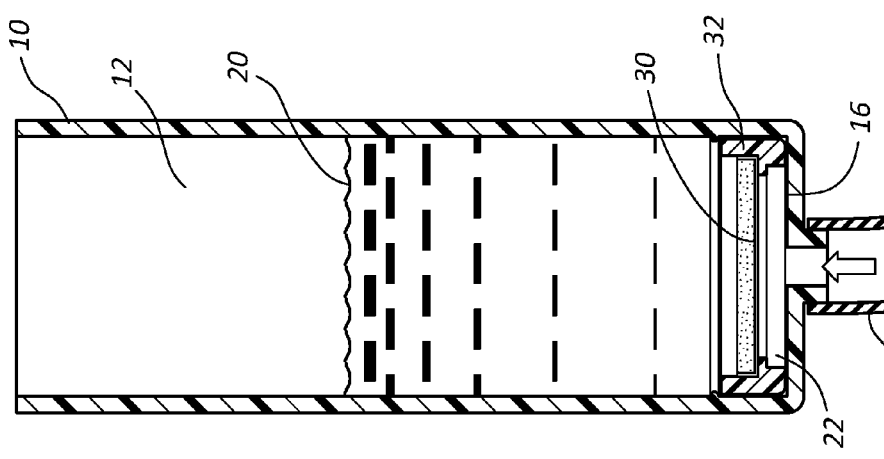
FIG. 1B
(Prior Art)
FIG. 1A
(Prior Art)

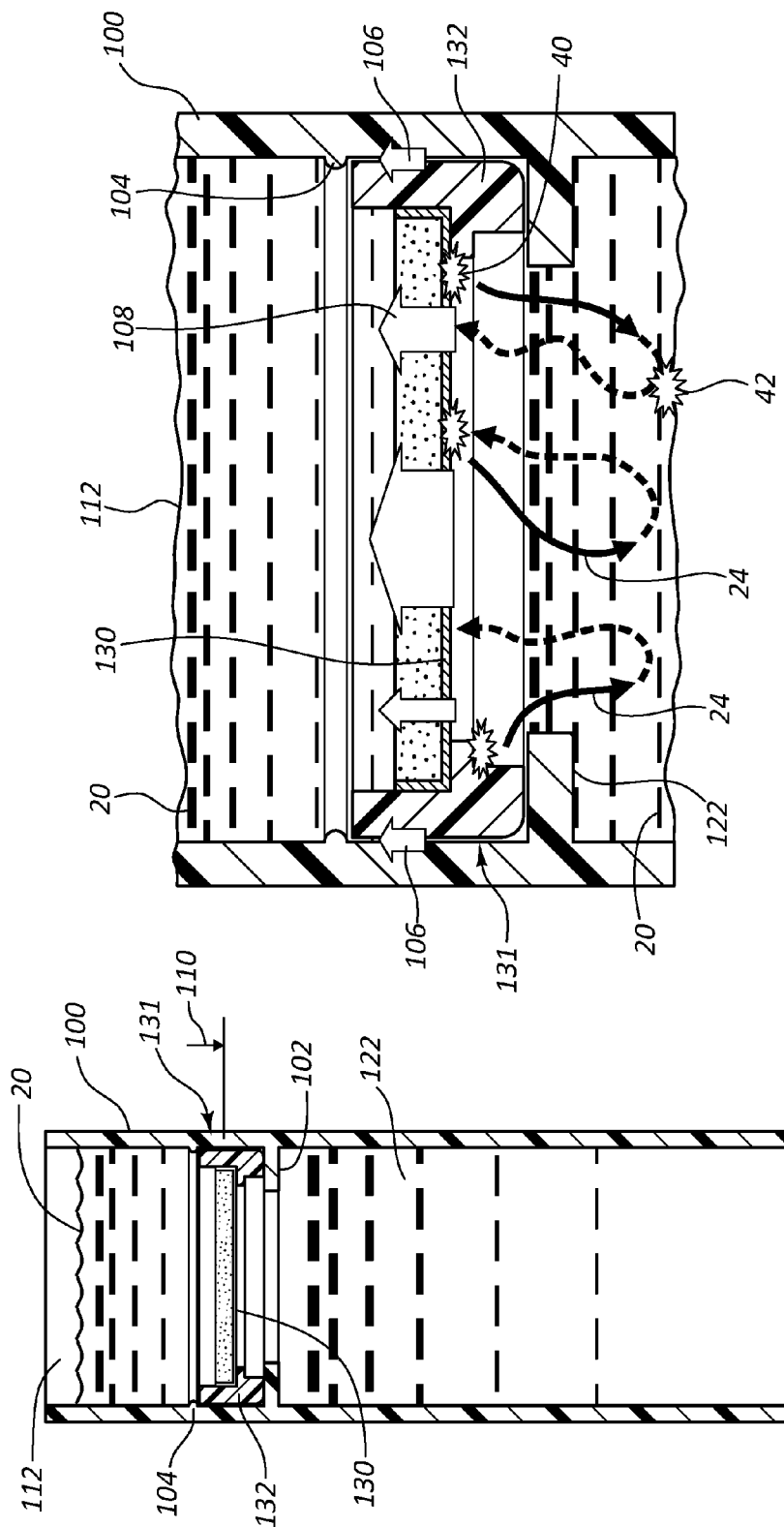

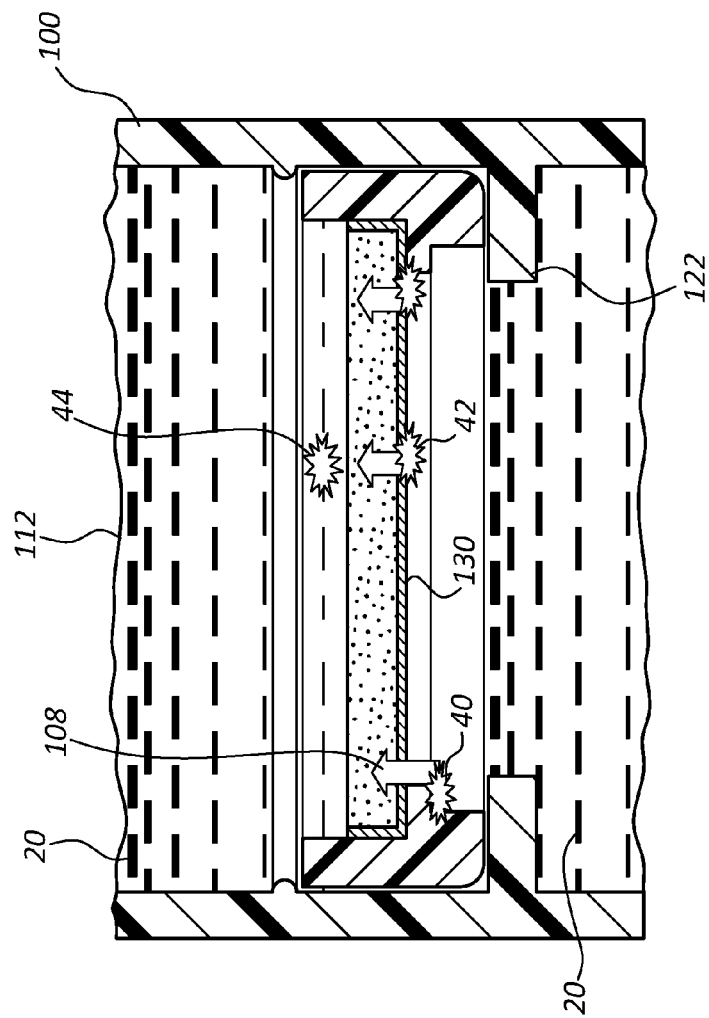
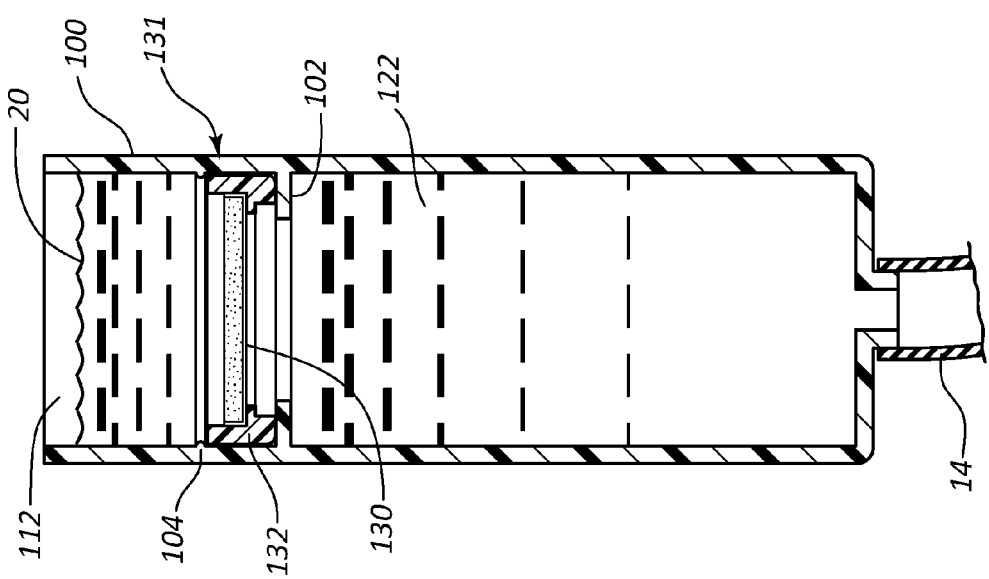
FIG. 3A
FIG. 3B

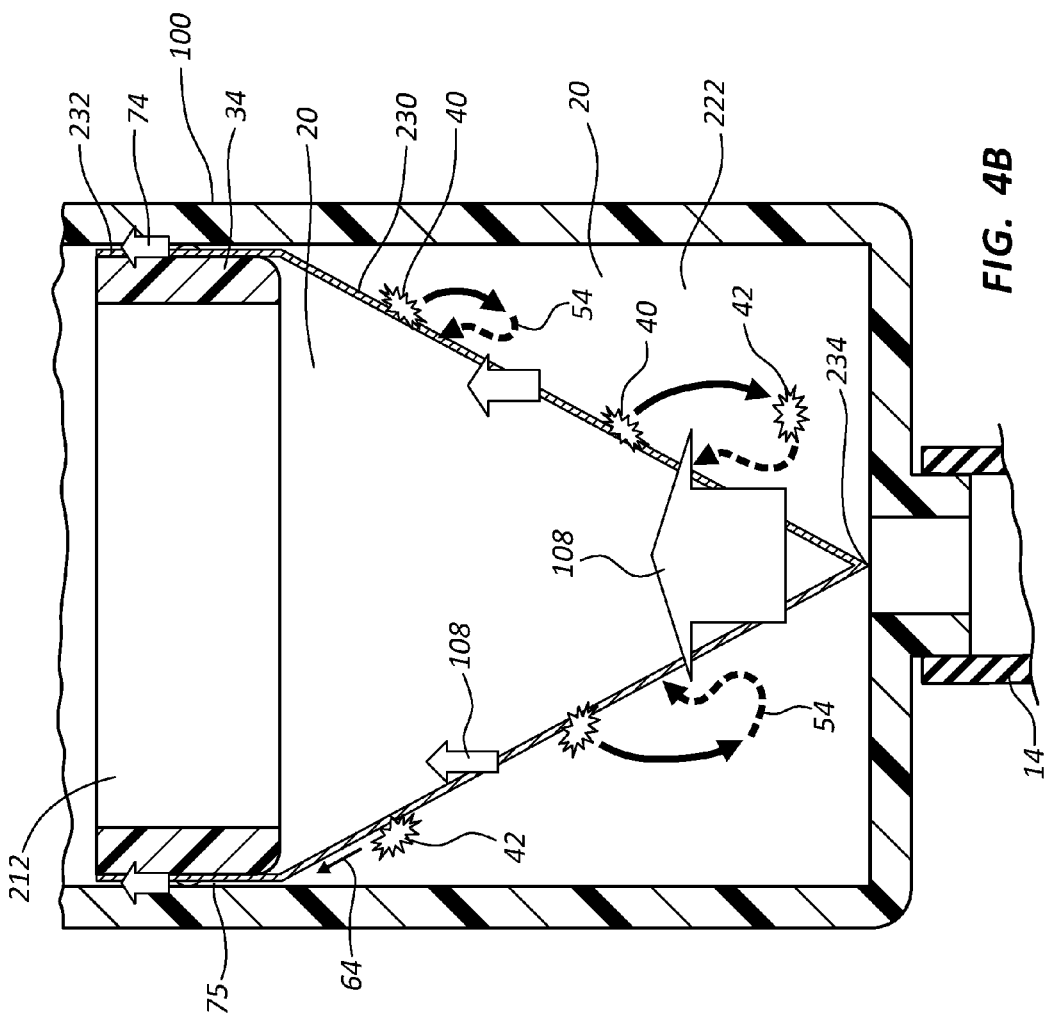
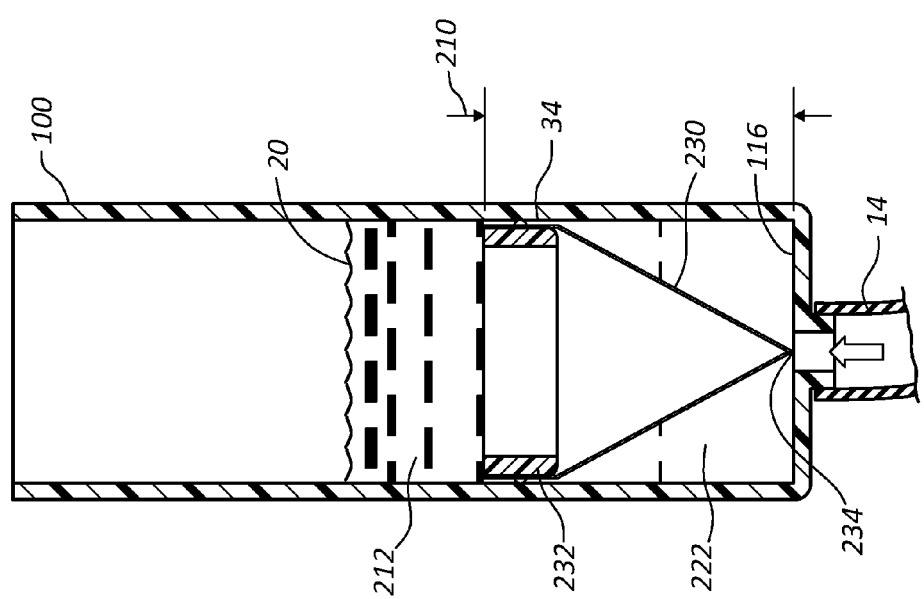
FIG. 4A
FIG. 4B

IV DRIP CHAMBER WITH FILTER AND BOTTOM RESERVOIR

BACKGROUND OF THE INVENTION

This invention relates generally to tubing sets used in the administration of liquids to a patient that are commonly referred to as intravenous ("IV") sets and more particularly concerns bubble free, self-priming IV sets. An IV set according to the invention is used broadly herein to describe tubing sets used in the arterial, intravenous, intravascular, peritoneal, and non-vascular administration of fluid. Of course, one of skill in the art may use IV set to administer fluids to other locations than those listed within a patient's body.

One common method of administering fluids into a patient's blood flow is through an IV set. An IV set is an apparatus that generally includes a connector for connection to a fluid reservoir or IV bag, a drip chamber used to determine the flow rate of fluid from the fluid reservoir, an intravenous fluid line for providing a connection between the fluid reservoir and the patient, and a catheter that may be positioned intravenously in a patient. An IV set may also include a Y-connector that allows for the piggybacking of IV sets and for the administration of medicine from a syringe into the tubing of the IV set.

It is a generally good practice to remove air from IV sets which access a patient's blood flow. While this concern is critical when accessing arterial blood, it is also a concern when accessing the venous side. Specifically, if air bubbles are allowed to enter a patient's blood stream while receiving the intravenous administration of liquids, the air bubbles can form an air embolism and cause serious injury to a patient.

Normally, in a majority of adults, the right atrium and the left atrium are completely separated from each other so that the blood and air bubbles are moved from the right atrium, to the right ventricle, and then to the lungs where the air bubbles may be safely vented. The bubble free blood is then returned to the left atrium, where the blood is moved to the left ventricle and then sent throughout the body.

However, in infants and in a small portion of the adult population, the right atrium and left atrium are not completely separated. Consequently, air bubbles can move directly from the right atrium into the left atrium and then be dispersed throughout the body. As a result, these air bubbles may cause strokes, tissue damage, and/or death. Therefore, it is important to prevent air bubbles from entering a patient's blood stream.

In spite of the importance of removing air bubbles while priming an IV set for use in the intravenous administration of liquids, the complete removal of air bubbles can be a time consuming process. The process may also lead to contamination of the IV set by inadvertently touching a sterile end of the IV set. Typically, when an IV set is primed, a clamp is closed to prevent liquid from moving from a drip chamber through the tubing. The IV set is then attached to an IV bag or bottle. Once attached, the drip chamber, which is typically made of a clear flexible plastic, may be squeezed to draw the liquid out of the IV bag or bottle and into the drip chamber. The drip chamber is allowed to fill about ⅓ to ½ full when the clamp is opened to allow liquid to flow through the tube to an end of the IV set.

This initial process, however, typically traps air in tubing which must be removed. For example, the flow of the liquid through the tubing of the IV set may be turbulent and can entrap air within the tube as the boundary layer between the liquid and the tubing is sheared. The flow rate out of the drip chamber may be higher than the flow rate of liquid entering the drip chamber. This can cause a bubble ladder to form as air is sucked from the drip chamber into the tubing.

Additionally, air bubbles may be generated as drops of liquid strike the surface of the pool of liquid within the drip chamber. These air bubbles can be pulled into the tubing of the IV set from the drip chamber. This problem may be aggravated in pediatric applications where the drip orifice may be smaller which may result in increased turbulence.

To remove air bubbles from the IV set, liquid from the IV bag or bottle is allowed to flow through the tubing while an attendant taps the tubing to encourage the air bubbles out the end of the IV set. As the liquid is allowed to flow out of the IV set to clear air bubbles from the tubing, the liquid is generally allowed to flow into a waste basket or other receptacle. During this procedure the end of the tubing may contact the waste basket or be touched by the attendant and thus, become contaminated. An additional shortcoming of this debubbling process is that it requires attention and time that could have been used to perform other tasks that may be valuable to the patient.

Another debubbling method is to directly remove air bubbles from the IV set. More specifically, if the IV set includes a Y-connector, air bubbles may be removed at the Y-connector by a syringe.

In some cases, a small pore filter may be used in the drip chamber to prevent air from entering the IV tubing from the drip chamber. However, the bubbles formed from the dripping action may become trapped on the filter, thus, reducing the flow of liquid through the filter to the IV tubing. However, the filter is normally positioned so that air bubbles become trapped between the bottom of the filter and the bottom surface of the drip chamber. As the fluid flows out of the drip chamber, these trapped air bubbles may become dislodged, exit the drip chamber, and be infused into the patient.

Thus, while systems and methods currently exist to prevent the infusion of air bubbles to a patient, challenges still exist. Accordingly, it would be an improvement in the art to augment or replace current techniques with improved system and methods. Such improved system and methods are provided herein.

BRIEF SUMMARY OF THE INVENTION

The apparatus of the present invention has been developed in response to the present state of the art, and in particular, in response to the problems and needs in the art that have not been fully solved by currently available IV sets. Thus, the present invention provides an IV set for use in intravenous administration of liquids that prevents air from being passed to a patient during the intravenous administration of liquids.

In accordance with the invention as embodied and broadly described herein in the preferred embodiment, an IV set is provided. According to some implementations, an IV set may include a drip chamber having an upper reservoir that is separated from a lower reservoir via a filter assembly. The filter assembly includes an air filter and one or more filter brackets that are configured to secure and maintain a position of the air filter in the drip chamber. The drip chamber further includes a bottom surface that is configured to receive or support an intravenous fluid line that is configured to access the vasculature of a patient. The drip chamber may further include a spike or other inlet that permits the drip chamber to access a fluid that is stored in an IV bag or bottle. In some instances, at least one of the upper and lower reservoirs are capable of being squeezed to increase fluid pressure therein.

The distance between the filter assembly and the bottom surface is selected to prevent dislodged air bubbles from being drawn into the intravenous fluid line during an infusion procedure. Generally, this distance is selected by determining the height above the bottom surface at which the suction force of fluid leaving the bottom reservoir via the intravenous fluid line is less than the buoyancy of the air bubbles that become dislodged from the air filter. The placement of the filter assembly may therefore result in the upper reservoir having a volume that is less than the volume of the lower reservoir. The placement of the filter assembly may alternatively result in the upper reservoir having a volume that is greater than a volume of the lower reservoir. Further, the placement of the filter assembly may results in the upper reservoir having a volume that is approximately equal to a volume of the lower reservoir.

In some implementations of the present invention, the air filter comprises a conical filter having a cylindrical base that is secured to the inner surface of the drip chamber via a filter bracket. The conical filter is positioned such that the tip of the conical filter is adjacent to the bottom surface of the drip chamber. In some instances, it is desirable to provide a distance between the tip of the conical filter and the bottom surface.

Some implementations of the present invention further include a method for preventing a dislodged air bubble from being drawn into an intravenous fluid line of an intravenous infusion assembly during an infusion procedure. This method includes a step for providing a drip chamber having an upper reservoir separated from a lower reservoir via a filter assembly. The drip chamber further includes a bottom surface configured to receive an intravenous fluid line. The method further includes positioning the filter assembly at a distance from the bottom surface, wherein the distance is configured to prevent an air bubble dislodged from the filter assembly from being drawn into the intravenous fluid line during an infusion procedure.

The method may further include a step for agitating the drip chamber to dislodge bubbles from an air filter of the filter assembly. Some implementations further include a step for occluding the intravenous fluid line, such as by pinching, and simultaneously squeezing the lower reservoir. The act of squeezing the lower reservoir increases the fluid pressure within the lower reservoir to force dislodged air bubbles through the air filter and into the upper reservoir. Some methods of the present invention may further include a step agitating the drip chamber while simultaneously occluding the intravenous fluid line and squeezing the lower reservoir.

Some implementations of the present invention further include an intravenous infusion assembly having a drip chamber which includes an upper reservoir separated from a lower reservoir via a filter assembly, wherein the drip chamber further includes a bottom surface configured to receive or otherwise support an intravenous fluid line. The drip chamber further includes a distance interposed between the filter assembly and the bottom surface, wherein the distance is configured to prevent an air bubble dislodged from the filter assembly from being drawn into the intravenous fluid line during an infusion procedure. The intravenous infusion assembly further includes an air filter forming a portion of the filter assembly. The air filter may include a flat, disc-shaped filter, a cylindrical filter, or a conical-shaped filter. The intravenous infusion assembly further includes a section of intravenous fluid line coupled to the bottom surface of the drip chamber, wherein the section of intravenous fluid line is configured to access the vasculature of a patient.

These and other features and advantages of the present invention will become more fully apparent from the following description and appended claims, or may be learned by the practice of the invention as set forth hereinafter.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 1, shown in parts A and B is a cross-section view of a PRIOR ART drip chamber;

FIG. 2, shown in parts A and B is cross-section view of a drip chamber having a bottom reservoir and demonstrating the displacement of trapped air bubbles when the drip chamber is agitated in accordance with a representative embodiment of the present invention;

FIG. 3, shown in parts A and B is a cross-section view of a drip chamber having a bottom reservoir and demonstrating the displacement of trapped air bubbles when the IV line is occluded via pinching and the bottom reservoir is squeezed in accordance with a representative embodiment of the present invention; and FIG. 4, shown in parts A and B is a cross-section view of a drip chamber having a bottom reservoir and a conical filter, and demonstrating the displacement of trapped air bubbles when the drip chamber is agitated in accordance with a representative embodiment of the present invention.

DETAILED DESCRIPTION OF THE INVENTION

The presently preferred embodiments of the present invention will be best understood by reference to the drawings, wherein like parts are designated by like numerals throughout. It will be readily understood that the components of the present invention, as generally described and illustrated in the figures herein, could be arranged and designed in a wide variety of different configurations. Thus, the following more detailed description of the embodiments of the IV drip chamber with filter and bottom reservoir of the present invention, as represented in FIGS. 1A through 4B, is not intended to limit the scope of the invention, as claimed, but is merely representative of presently preferred embodiments of the invention.

For this application, the phrases "connected to," "coupled to," and "in communication with" refer to any form of interaction between two or more entities, including mechanical, electrical, magnetic, electromagnetic, and thermal interaction. The phrase "attached to" refers to a form of mechanical coupling that restricts relative translation or rotation between the attached objects.

The phrase "attached directly to" refers to a form of attachment by which the attached items are either in direct contact, or are only separated by a single fastener, adhesive, or other attachment mechanism. The term "abutting" refers to items that are in direct physical contact with each other, although the items may not be attached together. The terms "integrally formed" refer to a body that is manufactured integrally, i.e., as a single piece, without requiring the assembly of multiple pieces. Multiple parts may be integrally formed with each other if they are formed from a single work piece.

Referring now to FIGS. 1A and 1B, a PRIOR ART drip chamber 10 is shown. Drip chamber 10 is commonly used as part of an infusion system for delivering a fluid to a patient via an intravenous catheter or needle (not shown). Drip chamber 10 is also commonly coupled to an IV bag via a spike (not shown) or another type of connection known by those of skill in the art.

Drip chamber 10 may include a reservoir 12 that is configured to receive and store a volume of fluid 20 from an IV bag. The volume of fluid 20 collects in reservoir 12 preparatory to exiting reservoir 12 and drip chamber 10 into an intravenous line 14 coupled to a patient.

In some instances, an air filter 30 is disposed at the bottom of reservoir 12. Air filter 30 is configured to prevent passage of air bubbles 40 from reservoir 12 into intravenous line 14 during an infusion procedure. In some devices, air filter 30 is retained within reservoir 12 via a filter bracket 32. Generally, filter bracket 32 is configured to place air filter 30 at a position proximate to the bottom 16 of drip chamber 10. As such, the majority of reservoir 12 and fluid 20 is located above air filter 30. In some instances, filter bracket 32 is configured to minimize the distance between air filter 30 and bottom 16 of drip chamber 10, thereby providing a minimum volume of fluid 22 between air filter 30 and bottom 16.

Prior to infusing a fluid into a patient, it is common practice to prime drip chamber 10 to remove air bubbles from intravenous fluid line 14, air filter 30, minimum volume of fluid 22, and intravenous fluid line 14. Following the priming procedure, air bubbles 40 are commonly trapped at various positions along filter bracket 32 and air filter 30 within the minimum volume of fluid 22. Typical procedures for removing air bubbles 40 are generally unsuccessful, such as agitating or twirling drip chamber 10. However, during the infusion procedure, air bubbles 40 are commonly dislodged 24 by fluid 20 passing through air filter 30. The dislodged air bubbles 42 quickly flow out of drip chamber 10, into intravenous fluid line 14, and into the patient. Although dislodged air bubbles 42 are less dense than fluid 22, the proximity of air filter 30 to intravenous fluid line 14 and the suction force of fluid leaving drip chamber 100 causes dislodged air bubbles 42 to be drawn into fluid line 14. This provides an undesirable result.

Various embodiments of the present invention provide a drip chamber 100 that overcomes the undesirable limitations of PRIOR ART drip chamber 10, shown in FIGS. 1A and 1B. In particular, some embodiments of the present invention provide a drip chamber 100 having an upper reservoir 112 and a lower reservoir 122. Upper and lower reservoirs 112 and 122 are separated by air filter 130. In some embodiments, air filter 130 comprises a particulate filter configured to prevent passage of particulates into intravenous fluid line 14. In other embodiments, air filter 130 comprises a hydrophilic material which is configured to prevent lower reservoir 122 from running dry. For example, in some instances the hydrophilic bond between fluid 20 in lower reservoir and air filter 130 prevents fluid from exiting lower reservoir 122 into intravenous fluid line 14 when upper reservoir 112 runs dry. Air filter 130 may further act as a flow restrictor to limit the flow of fluid 20 through drip chamber 100.

In some embodiments, drip chamber 100 comprises a mid-shelf 102 that provides a surface on which an air filter assembly 131 is supported. Air filter assembly comprises one or more filter brackets 132 that are configured to secure an air filter 130 at a desired position between upper and lower reservoirs 112 and 122. Drip chamber 100 may further include an annular protrusion 104 to further secure the position of filter bracket 132. One skilled in the art will appreciate that the position of air filter 130 in drip chamber 100 may be accomplished by various compatible systems and methods within the spirit of the present disclosure.

Upper reservoir 112 may comprise any desired volume of fluid 20. In some embodiments, upper reservoir 112 comprises a volume sufficient to permit a desire flow of fluid 20 through drip chamber 100 while maintaining a constant volume of fluid 20 in upper reservoir 112. Thus, air filter 130 remains constantly interposed between fluid 20 in upper reservoir 112 and lower reservoir 122 during an infusion procedure.

Lower reservoir 122 is defined as the portion of drip chamber 100 that is located between mid-shelf 102, or air filter 130, and bottom surface 116. Lower reservoir 122 comprises a volume which provides a distance between air filter 130 and intravenous fluid line 14. This lower reservoir 122 is filled with fluid 20 during a priming procedure in advance of an infusion procedure. In some embodiments, trapped air bubbles 40 within lower reservoir 122 are dislodged 24 from air filter 130 and filter bracket 132 by agitating drip chamber 100. The dislodged air bubbles 42 flow into lower reservoir 122, as shown. The dislodged air bubbles 42 are less dense than fluid 20 in lower reservoir 122. As such, the dislodged air bubbles flow back up to air filter 130 and are passed through air filter 130 and into upper reservoir 112. Further, the distance 110 between air filter 130 and bottom surface 116 prevents the dislodged air bubbles 42 from being drawn into intravenous fluid line 14, as occurs in the PRIOR ART devices.

In some instances, dislodged air bubbles 42 are redirected to travel 106 between filter bracket 132 and the inner wall of drip chamber 100. In other embodiments, dislodged air bubbles 42 flow 108 back through air filter 130. However, in some embodiments, dislodged air bubbles 42 reestablish contact with air filter 130 while still being positioned in lower reservoir 122, as shown in FIGS. 3A and 3B. For these instances, dislodged air bubbles 42 may be forced through 108 air filter 130 by squeezing lower reservoir 122 after occluding intravenous fluid line 14 via pinching, or another technique. The process of squeezing lower reservoir 122 increases fluid pressure therein and forces dislodged air bubbles 42 to pass through air filter 130.

In some instances, the process of occluding intravenous fluid line 14 and squeezing lower reservoir 122 is further combined with agitating drip chamber 100. The combination of these actions achieves full dislodgement of trapped air bubbles 40 and allows dislodged air bubbles 42 to pass through air filter 130 and into upper reservoir 112. The filtered air bubbles 44 then continue to rise through fluid 20 in upper reservoir 112.

In some embodiments, drip chamber 100 alternatively comprises a conical air filter 230, as shown in FIGS. 4A and 4B. Conical air filter 230 may comprise any material capable of filtering bubbles 40 from fluid 20. In some embodiments, conical air filter 230 comprises a cylindrical base 232 having a diameter that is approximately equal to a diameter of drip chamber 100. The cylindrical base 232 is secured to the inner surface of drip chamber 100 via a filter bracket 34. In some instances, cylindrical base 232 is positioned at a height 210 above bottom 116 of drip chamber 100 so that the tip 234 of filter 230 is positioned approximately at bottom 116.

Conical filter 230 divides drip chamber 100 into an upper reservoir 212 and a lower reservoir 222. The conical shape of filter 230 reduces the volume of lower reservoir 222 and increases the volume of upper reservoir 212. The conical shape of filter 230 positions a minimum surface area of filter 230 (i.e. tip 234) at a position adjacent to patient fluid line 14. The remaining surface areas of filter 230 are positioned at greater distances from fluid line 14. In some instances, the conical shape of filter 230 exponentially positions the remaining surfaces of filter 230 at increasing distances from fluid line 14. Thus, where the number of air bubbles 40 corresponds to the surface area of filter 230, the largest amount of air bubbles 40 will be positioned at the greatest distance from fluid line 14. Thus, the conical shape of filter 230 reduces the risk of dislodged air bubbles 42 from being drawn into intravenous fluid line 14.

The conical shape of filter 230 further provides an angled surface to assist in dislodging air bubbles 40 as part of a priming procedure. For example, in some embodiments the angled surface of filter 230 reduces the coefficient of friction between bubbles 40 and filter 230. This feature reduces the amount of agitation needed to dislodge bubbles 40 from filter 230. Further, in some embodiments bubbles 40 that become dislodged 42 during an infusion procedure are redirected 54 towards filter 230 as they are drawn towards intravenous fluid line 14. The dislodged bubbles 42 then re-contact filter 230 and pass through 108 into upper reservoir 212. In other embodiments, an infusion procedure is temporarily suspended while drip chamber 100 is agitated, and/or squeezed while occluding intravenous fluid line 14.

In other embodiments, bubbles 42 that are dislodged during an infusion procedure are sufficiently distanced from intravenous fluid line 14 so that the buoyancy of the bubble is greater than the suction force of fluid 20 exiting lower reservoir 212 via intravenous fluid line 14. As such, the dislodged air bubbles 42 travel upwardly 64 along conical filter 230. In some instances, the dislodged air bubbles 42 pass through the angled surface of conical filter 230 as they move upwardly 64 towards cylindrical base 232. In other embodiments, the dislodged air bubbles 42 move upwardly 64 to cylindrical base 232 where they pass into upper reservoir 212 by traveling 74 between cylindrical base 232 and the inner surface of drip chamber 100. In some instances, bubbles 42 travel between cylindrical base 232 and the inner surface of drip chamber 100 via gap 75.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. A drip chamber for controlling the flow rate of fluid within an intravenous infusion assembly, comprising:
    a filter assembly positioned within the drip chamber to divide the drip chamber into an upper reservoir closer in proximity to an inlet of the drip chamber than an outlet of the drip chamber and having a first volume and a lower reservoir closer in proximity to the outlet of the drip chamber than the inlet and having a second volume, the filter assembly including a small pore filter;
    a bottom surface having an opening through which the fluid flows out from the lower reservoir, the bottom surface configured to receive an intravenous fluid line; and
    a gap between the filter assembly and an inner wall of the drip chamber device, the gap configured to allow air bubbles to pass through the gap from the lower reservoir to the upper reservoir, wherein the small pore filter is spaced at a distance from the bottom surface, the distance being configured such that the downward suction force caused by the fluid as it passes through the opening in the bottom surface that is applied to air bubbles in contact with the small pore filter is less than the upward force caused by the buoyancy of the air bubbles thereby preventing the air bubbles, once dislodged from the small pore filter, from being drawn into the intravenous fluid line during an infusion procedure.

2. The device of claim 1, wherein the second volume is greater than the first volume.

3. The device of claim 1, wherein the filter assembly further comprises a filter bracket.

4. The device of claim 1, wherein the small pore filter comprises a conical filter.

5. The device of claim 4, wherein the first volume is greater than the second volume.

6. The device of claim 1, further comprising an inner surface having a mid-shelf on which the filter assembly is supported.

7. The device of claim 1, wherein the small pore filter is hydrophilic.

* * * * *